United States Patent [19]

Stumpf et al.

[11] Patent Number: 4,998,433

[45] Date of Patent: Mar. 12, 1991

[54] METHOD AND MEANS FOR CONDENSING TRACE AIR CONTAMINATES FROM GASES

[76] Inventors: David K. Stumpf, 630 LaCholla Blvd., Tucson, Ariz. 85745; Curt N. Blair, 2302 N. Catalina Ave., Tucson, Ariz. 85712

[21] Appl. No.: 367,963

[22] Filed: Jun. 19, 1989

[51] Int. Cl.$^5$ ............................................. G01N 30/12
[52] U.S. Cl. .............................. 73/25.01; 73/863.110; 422/89
[58] Field of Search ................. 73/25, 863.11; 422/70, 422/89

[56] References Cited

U.S. PATENT DOCUMENTS 4,312,835 1/1982 Zoltan et al. ...................... 73/863.11

Primary Examiner—John Chapman
Assistant Examiner—Joseph W. Roskos
Attorney, Agent, or Firm—Shlesinger Fitzsimmons Shlesinger

[57] ABSTRACT

A metallic sample block has formed therein a serpentine shaped duct containing glass beads. The block is secured in thermally conductive contact with a thermoelectric element to which voltage of one polarity is applied to chill the block to a range of approximately −25° C. to −90° C. When the block temperature has been lowered sufficiently a gas sample is conveyed in one direction through the duct causing contaminates therein to be condensed out on the beads. Thereafter the polarity of the voltage applied to the thermoelectric element is reversed to cause it to heat the block and vaporize the previously condensed contaminates, after which a carrier gas is conveyed in the opposite direction through the duct to a gas analyzer device.

16 Claims, 3 Drawing Sheets

METHOD AND MEANS FOR CONDENSING TRACE AIR CONTAMINATES FROM GASES

BACKGROUND OF THE INVENTION

This invention relates to chromatography, and more particularly to an improved method and cryogenic means for condensing trace air contaminates for delivery to a gas chromatograph column or the like. Even more particularly, this invention relates to improved means of the type described which is particularly suited for use in a laboratory or in the field.

As noted by Messrs. Brettell and Grob in their articles entitled Cryogenic Techniques In Gas Chromatography (Part One), in the October, 1985 issue of American Laboratory (pp. 19–32) and Part Two: Cryofocusing And Cryogenic Trapping, in the November, 1985 issue of this publication (pp. 50–66) it has long been customary in gas chromatography (GC) to utilize a cryogenic means for trapping or condensing trace contaminates out of a gaseous phase. Typically such cryogens have been liquid gases, such as liquid argon, liquid carbon dioxide or liquid nitrogen. The gas containing the contaminate is circulated through, for example a U-shaped tube containing small glass beads, or the like. The tube is immersed in the liquid cryogen, thereby causing trace contaminates to be condensed out o the gas onto the glass beads. Thereafter the tube is heated and the contaminate is revaporized and fed to the GC.

One of the principal advantages of using a liquid cryogen is its ability to lower the temperature well below ambient, for example to as low as $-196°$ C. in the case of liquid nitrogen. A primary disadvantage of liquid cryogens, however, is that they are dangerous to work with and require very cumbersome and heavily insulated handling and storage apparatus. Moreover, the liquid cryogen is consumable during use, and the sampling cycle can be very time consuming, so that liquid cryogenics have proved to be difficult and expensive to use.

In the past, a variety of cooling devices have employed heat pumps of the type based on thermoelectricity (Peltier effect). See, for example, U.S. Pat. Nos. 4,764,193, 4,744,220, 4,726,193 and U.S. Pat. No. 4,782,664. Moreover, although at least one author has suggested that such pumps could be used for cooling a GC oven, thermoelectric heat pumps have not been considered for GC sampling or trapping applications.

It is an object of this invention, therefore, to provide an improved method and apparatus of separating out and concentrating trace contaminates from gases such as air, or the like, thereby considerably simplifying cryogenic gas trapping (CGT) procedures.

A further object of this invention is to provide improved CGT apparatus of the type described which considerably reduces the size and the cost of the equipment heretofore employed for condensing trace contaminates from gaseous mixtures, or the like. Still another object of this invention is to provide improved cryogenic gas sampling apparatus of the type described which is particularly adapted for use in a laboratory surrounding, or which can be made portable to permit ready collection of contaminate samples in the field.

Other objects of the invention will be apparent hereinafter from the specification and from the recital of the appended claims, particularly when read in conjunction with the accompanying drawings.

SUMMARY OF THE INVENTION

The apparatus includes a gas trapping or sampler module, a pneumatic module for drawing a gas sample through the sampler module, and a combined power controller module for operating the apparatus. The trapping apparatus comprises a multi-stage, thermoelectric heat pump in the form of at least two Peltier-type chips clamped on a heat sink beneath a metal sampler block having therein a serpentine-shaped duct. In the laboratory embodiment a multi-port sampling valve (six ports in the illustrated embodiment) is used to switch the apparatus between a sampling mode and a transfer mode.

During a sampling mode or cycle the heat pump chips are energized to reduce the temperature of the sampler block to $-50°$ C. or the like. The pneumatic module then evacuates a reference enclosure, the volume of which depends upon the type of gas sample that is sought. When the reference volume has been evacuated, the pneumatic module connects the vacuum in the reference volume through the sample valve and the serpentine duct in the sampler block with a supply of the gas to be sampled. The gas sample is then drawn through the chilled duct to the reference enclosure, at which time contaminates are condensed out on glass beads in the serpentine duct.

When the reference volume has been filled, the sampler valve is switched to a transfer mode, and the power to the heat pump chips is reversed so that they now heat the sampler block and return the condensed contaminants to gaseous form. At this time the sampler block is cut off from the pneumatic module and its duct is connected instead at one end to a supply of a carrier gas, and at its opposite to a gas analytical device, such as a GC oven into which the contaminants are conveyed by the carrier gas, and in a direction opposite to that in which the sample gas entered the duct.

The sample block may be removably mounted on the heat pump chips for use with portable such apparatus in the field.

THE DRAWINGS

DETAILED DESCRIPTION OF THE PREFERRED EMBODIMENTS

Figure 1:
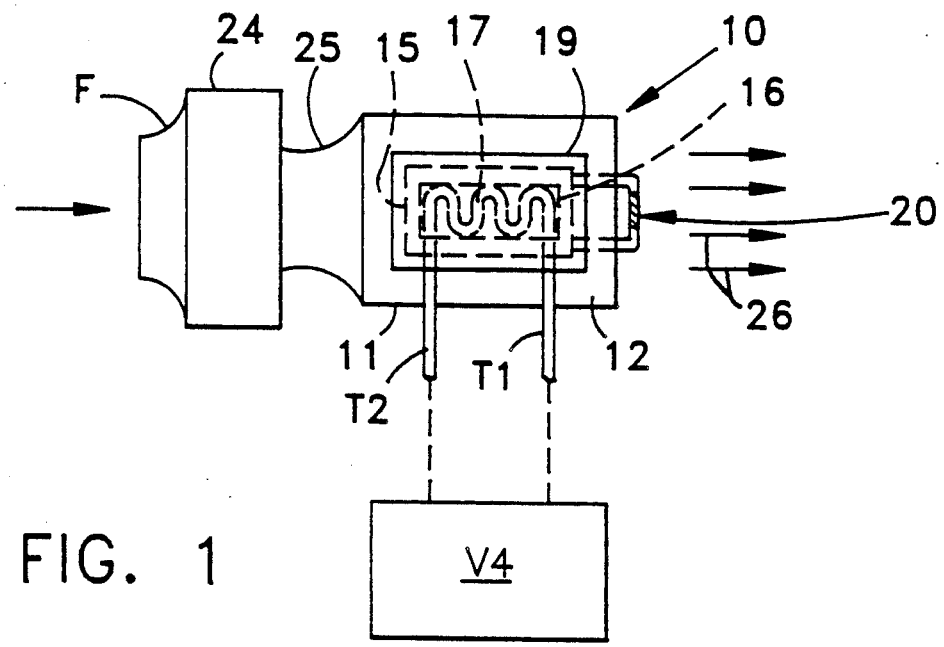
FIG. 1 is a fragmentary plan view of a portion of the cryogenic gas sampler apparatus made according to one embodiment of this invention, and with a portion of an associated clamping device broken away and shown in section.

Referring now to the drawings by numerals of reference, and first to FIGS. 1 to 3, 10 denotes generally a cryogenic gas sampling module comprising an aluminum heat sink 11 of generally conventional design, and having a plane upper surface 12 and a plurality of downwardly depending, spaced, parallel cooling fins 13. Secured by a thermally conductive interface, such as a thermally conductive film or grease, to the upper surface 12 of the heat sink 11, and with its plane bottom surface in nearly coplanar engagement with surface 12, is a flat, generally rectangularly shaped thermoelectric (Peltier) heat pump element or chip 15, which by way of example may be of the type sold by Materials Electronic Products Corp. of Trenton, N.J. under catalog No. CP1.4-127-06L. Also secured by a thermally conductive interface to the upper surface of the element 15 is a second thermoelectric heat pump element 16, which is similar to but slightly smaller than element 15. The plane bottom surface of element 16, of course, has substantially coplanar contact with the upper surface of the lower or larger heat pump element 15.

Also secured by a thermally conductive interface to the upper surface of the heat pump chip or element 16 in substantially coplanar engagement therewith is a sample block 17. In this embodiment block 17 is in the form of the serpentine-shaped section of a length of copper tubing, having opposite ends T1 and T2, respectively, which are adapted to be connected to a sampling valve V4 (FIG. 1) that is described in greater detail hereinafter. Block 17 and the two underlying chips 15 and 16 are insulated from the ambient atmosphere by a layer of insulation 18, which overlies and encloses the tube section or block 17 and the two chips 15 and 16, and which has a marginal portion thereof at its lower end engaged with the upper surface 12 of the heat sink 11. This insulation 18 in turn is enclosed within or covered by an inverted, generally rectangularly-shaped cover member 19, which is made from a ceramic material or the like.

Very close thermal contact is required as between the confronting surfaces of the heat sink 11, the chips 15 and 16, and the sample block 17. For this reason a compressive force is applied to the parts 11 and 15-17, such as for example in the form of a conventional quick-release clamp 20 having one jaw 21 overlying the cover member 19, and the other jaw 22 engaged with the bottom of heat sink 11.

Figure 2:
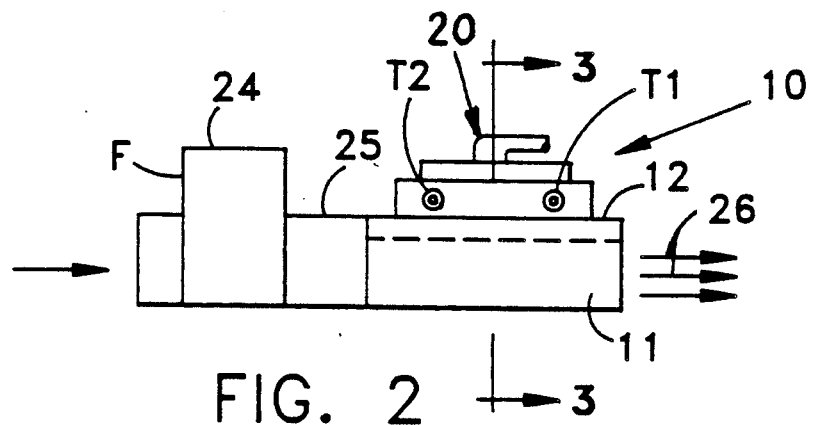
FIG. 2 is a fragmentary front elevational view of this apparatus.

As shown in FIGS. 1 and 2, the housing 24 of a cooling fan F has its outlet end 25 connected to one end of the heat sink 11 in order to blow cooling air between the fins 13 of the heat sink, and in the direction indicated by the arrows 26. Also as shown in FIG. 1, the ends T1 and T2 of the tubing extend out of the insulation 18 and cover 19 for connection to the apparatus used for conveying gas samples to and from, respectively, the serpentine sample block 17 of the tubing. Although not shown in the drawing, it will be apparent that at least section 17 of the tubing is packed with small glass beads on the order of 80/100 mesh, which provide condensing surfaces upon which the gas sample can be made to condense in block 17 as noted hereinafter.

Figure 4:
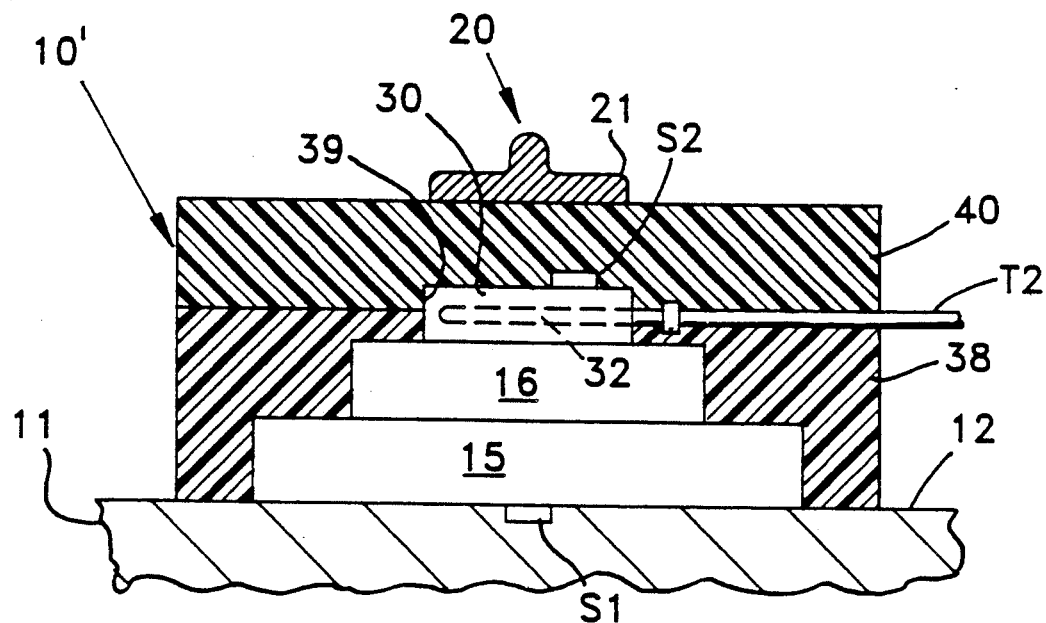
FIG. 4 is a greatly enlarged fragmentary sectional view generally similar to FIG. 3 but showing a modified for of this apparatus.
Figure 5:
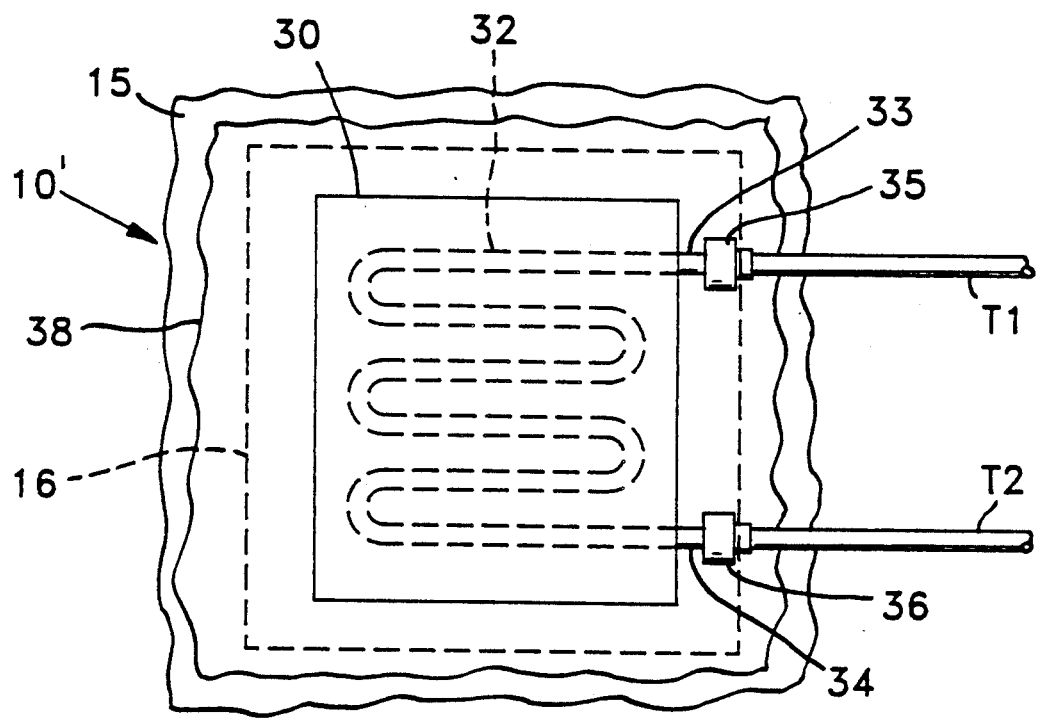
FIG. 5 is a slightly enlarged, fragmentary plan view of this modified apparatus, but with the clamping device removed.

Referring now to FIGS. 4 and 5, wherein like numerals are employed to denote elements similar to those employed in the first embodiment, 10' denotes generally a modified sampler module which is particularly suitable for use for the portable variety of this invention. As in the first embodiment, two thermoelectric chips or heat pump elements 15 and 16 are mounted one on top of the other on the upper surface 12 of the heat sink 11 so as to be in thermal contact with each other and with the heat sink. In this embodiment 30 denotes a flat, generally rectangularly-shaped sample block in the form of a copper plate, which has formed therein between its upper and lower surfaces a serpentine-shaped bore or conduit 32, opposite ends of which are connected to nipples 33 and 34 that project from one side of plate 30. The nipples 33 and 34 are releasably connected by conventional, quick-coupling fittings 35 and 36 to opposite ends T1 and T2, respectively, of the tubing. Also, although not illustrated, it will be understood that passage 32 in plate or block 30 is packed with glass beads which, as in the case of the first embodiment, are designed to form condensing surfaces for the gas that is fed to passage 32.

Also in this embodiment, the stacked thermoelectric 15 and 16 are enclosed within a surrounding, thermal insulating enclosure 38 having an upper end with overlies marginal portions of the chip 16, and which has in its upper surface a rectangular recess 39 for accommodating plate 30. The housing 38 in turn is closed by a removable cover 40, which is releasably secured by clamp 20 over plate 30, when the latter is secured on the upper surface of chip 16. Cover 40 may be made of substantially the same thermal insulation material as housing 38.

In practice, when the cover 40 is removed, the plate 30 may have its nipples 33 and 34 releasably connected to ends T1 and T2 of the tubing. It is then removably secured by a thermally conductive interface on the upper surface of the chip 16, and within the recess 39 of the insulating housing 38. The cover 40 is then clamped over the plate 30; and plate 30 then functions as a removable sampling block in which a sample of gas can be captured and condensed as noted hereinafter. In practice the fittings 35 and 36 will include normally-closed valves, which will be opened only when the ends T1 and T2 of the tubing are connected to the block or plate 30. As soon as the tubing is removed from fittings 34 and 35 the bore 32 becomes completely sealed, thus preserving any gas sample which was condensed therein.

A primary advantage of the apparatus as shown in FIGS. 4 and 5 is that it is particularly conducive to the production of portable sampling apparatus, when it is combined with the hereinafter described power/control and pneumatic modules. It then can be readily transported into the field where a portable DC power supply, such as gel cell battery or solar panel, can be utilized to supply the necessary electrical power for the unit.

Figure 6:
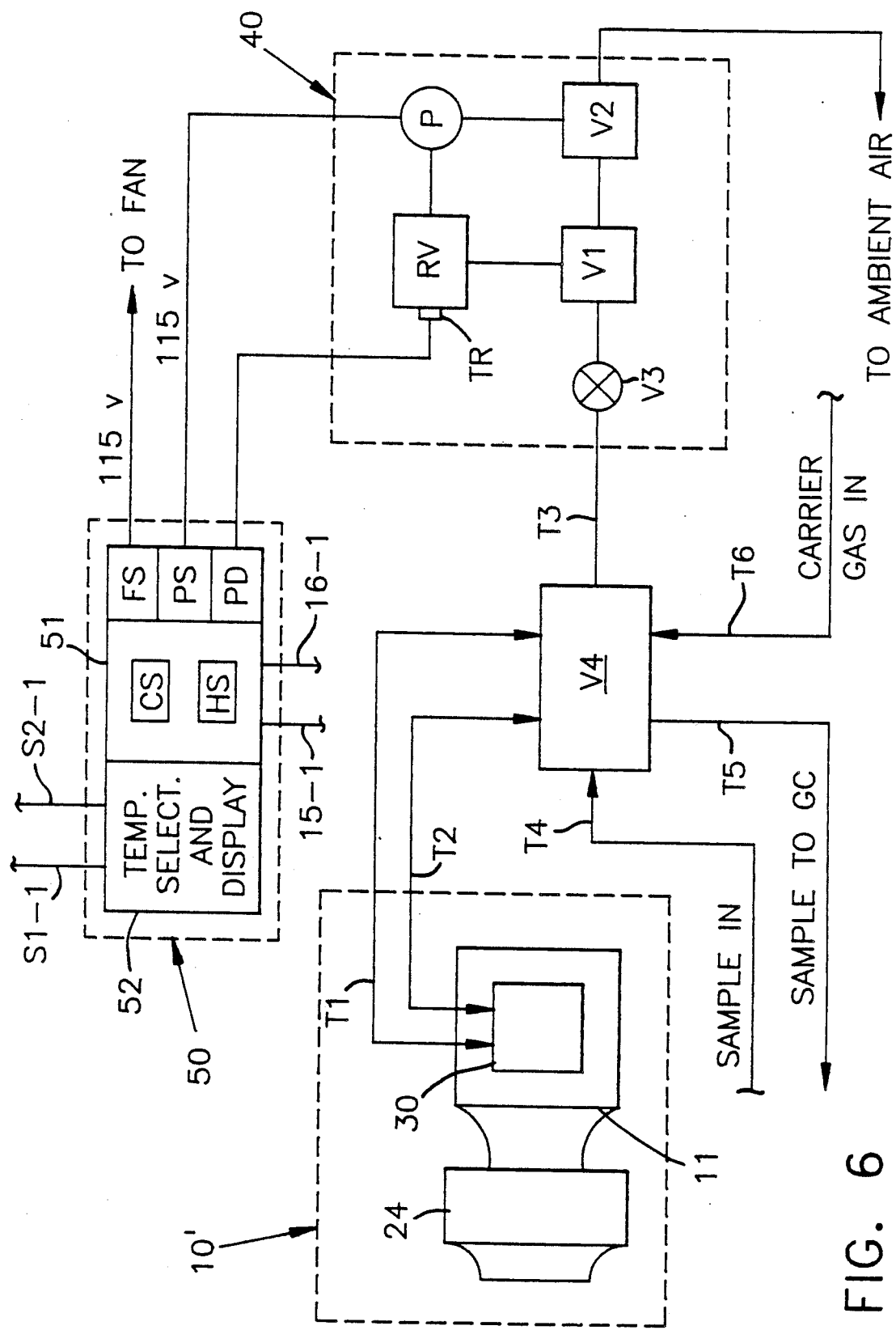
FIG. 6 is a combination pneumatic and wiring diagram illustrating schematically how gas is delivered to and from the sampling apparatus of this invention.

As shown in FIG. 6, the sampler module, for example the module 10', and the sampler valve V4 are adapted to be used in combination with a so-called pneumatic module 40, and a combined power supply/control module 50. In practice, the sampler valve V4 is a six port gas sampling valve, which may be of the type sold by Valco Instruments of Houston, Texas. As noted above, two of its ports (first and second ports thereof) are connected to tube ends T1 and T2, and a third port is connected by tubing T3 with the inlet of a flow control needle valve V3, which forms part of the pneumatic module 40.

Module 40 further includes a first three-way valve V1 having a first port connected to the output of valve V3, a second port connected to a reference volume enclosure RV, and a third port connected to the first port of a second three-way valve V2. A second port on valve V2 is connected to a vacuum pump P, and its third port (exhaust port) is connected to the ambient atmosphere.

Figure 3:
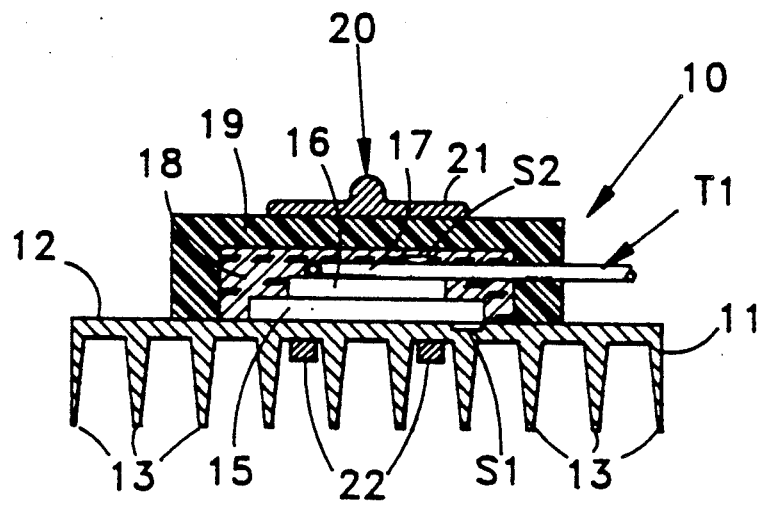
FIG. 3 is an enlarged, fragmentary sectional view taken generally along the line 3—3 in FIG. 2.

Still referring to FIG. 6, the fan F and the pump P are selectively connected through switches FS and PS, respectively, in the power supply/control module 50 with a 115 volt power supply (not illustrated). Module 50 contains a circuit 51 which is also connected to the above-noted 115 volt power supply to convert the AC power to the DC power necessary for operating the chips 15 and 16. Circuit 51 includes a chill switch CS and a heat switch HS that are operable for selectively supplying DC power through lines 15-1 and 16-1 to the heat pump elements 15 and 16, respectively. Module 50 contains also a temperature selecting and displaying circuit 52, which is connected through lines S1-1 and S2-1 to electrical temperature sensors S1 and S2, respectively, which as shown in FIGS. 3 and 4 are positioned to sense, respectively, the temperature of the heat sink 11 and the sample block 17 or 30.

In use, and assuming that AC power has been supplied to the module 50, the desired temperature to which the block 30 is to be chilled is selected by manipulating a temperature selecting switch (not illustrated) forming part of the circuit 52. The heat pump elements 15 and 16 are also energized by operation of the chill switch CS, so that the temperature of the block 30 begins to fall well below room temperature. At this time the fan switch FS is also operated so that the fan F directs cooling air through the spaces between the cooling fins 13 on the heat sink 11. By using the two stage heat pump represented by the chips 15 and 16, it is possible to reduce the temperature of the sample block 30 to the vicinity of $-50°$ C. By increasing the number of the heat pump stages, of course, this temperature can be lowered even further, for example to the vicinity of $-95°$ C. When the block 30 has reached the desired chill temperature, as indicated for example by the display portion of circuit 52, the associated sampling apparatus can be operated in one of two different ways, depending upon whether or not the sample is to be collected in a laboratory, or in the field by portable apparatus.

Assuming, for example, that the apparatus is located in a laboratory, after chip 30 has reached the desired chill temperature the sampling valve V4, which may be of the manually operated variety, is turned to a sampling position in which a sample supplying tube T4 is connected through a fourth port in valve V4, and through the valve and the second part thereof with the tubing end T2. The tubing end T1 is also connected at this time through the valve V4 and its first and third ports with the tubing T3. Also at this time, tubing T5, which leads to associated gas analytical apparatus, such as for example a gas chromatography (GC) oven, is connected to a fifth port in the sampling valve V4, and through the valve and its sixth port with tubing T6, which is utilized to supply a carrier gas to the sampling apparatus. At this time, therefore, the carrier gas is supplied through the sampling valve V4 to the GC oven, while the gas or air which is to be sampled (T4) is connected through the sample block 30, the tubing T3 and the needle valve V3 to the three-way valve V1.

Also at this time, valves V1 and V2 are adjusted manually, or otherwise, so that the first port of V1 is closed relative to valve V3, while its second and third ports are interconnected. Also the first and second ports of V2 are interconnected so that the enclosure RV representing the reference volume, which is user specific, is connected through the first and second ports of valve V2 to the inlet side of the vacuum pump P. At this time also, the third port in the valve V2, which is connected to the ambient atmosphere, is shut off; and the pump P is actuated by operation of the switch PS. Pump P therefore evacuates the reference volume RV until the pressure therein, as indicated by an electrical transducer TR, reaches a predetermined value. The transducer TR sends a signal to a pressure display PD in module 50, which therefore provides a visual indication of the pressure in RV. When the desired pressure is reached in RV the pump P can be shut off via its switch PS, or, the signal from the transducer TR can be used automatically to interrupt the power to the pump.

In any case, once the desired vacuum has been reached in the enclosure RV, valve V2 is turned so that its second and third ports are interconnected to exhaust the vacuum pump to the ambient atmosphere, and also to close its first port relative to valve V1. Sample collection is now initiated by turning valve V1 to cut off its third port from valve V2, and instead to interconnect its first and second ports, thus connecting the vacuum in the reference volume enclosure RV through valve V1, valve V3, tubing T3, valve V4, tubing T1, block 30, tubing T2 and valve V4 to the sample supply or inlet tubing T4. The vacuum in RV therefore draws the sample gas through the sample block 30 until such time that the pressure display PD, as monitored by the TR, indicates that the enclosure RV has been filled with the sample gas. During the filling of the enclosure RV the sample gas passes through the chilled block 30 where condensation occurs, the rate of flow of the gas through the block 30 and into the enclosure RV being controlled by the setting of the needle valve V3.

When the enclosure RV has been filled valve V1 is turned back to its original position in which it is blocked off from valve V3, and in which the reference volume RV is connected to the first port of V2. Also at this time, the chilling function of the chips 15 and 16 is terminated, and the heater switch HS is actuated in order to reverse the current flow to the chips 15 and 16, thereby causing them to perform a heating function, rather than a chilling function. Also at this time the sampler valve V4 is turned to a transfer position in which it connects the carrier gas tubing T6 to tubing T1, and connects tubing T2 to the tubing T5, which is connected to the GC oven. The heating of the block 30 and heat sink 11 again is monitored by the sensors S1 and S2; and this temperature is displayed by circuit 51 in the module 50. The heater temperature, incidentally, is preset as determined by experimental protocol by the particular sample which is being collected. As the block 30 warms up the previously condensed components (contaminants) vaporize or otherwise return to a gaseous form, and are conveyed to the GC oven by the carrier gas, which is now passing through block 30.

After the block 30 has reached and maintained a predetermined elevated temperature for a length of time determined by the nature of the sample which is being collected, the sampling valve V4 is once again returned to its gas sampling position in preparation for a repeat of the above-noted cycle. At this time the block 30 can be reused during the collection of another sample, or alternatively, a new sample block 30 can be inserted in place of the previously employed block.

If the apparatus is to be used in the field as portable apparatus, the sampling valve V4 is not employed. However, the sampling module 10 or 10', the pneumatic module 40 and the power supply/control module 50 are employed in a manner described above, with some exceptions. For example, the heating cycle is not employed; and the sample tubing T4 is connected to tubing T2 while tubing T3 is connected to tubing T1.

With the apparatus connected in this manner, the block 30 is first chilled by operating the switch CS and energizing the fan F. Valves V1 and V2 are then positioned to connect the enclosure RV with the inlet pump P, so that the enclosure is evacuated in a manner similar to that noted above. When display PD indicates that RV has been completely evacuated, the pump P is shut off from valve V1, and instead is connected to ambient air. Valve V1 is then manipulated to connect RV through V1, V3, T3, T1, the now-chilled block 30 and T2 with the sample inlet tubing T4, so that the sample is drawn through block 30 into RV. When the pressure of the latter reaches the correct value V1 is manipulated to disconnect RV from the block 30; and the quick disconnect couplings 35 and 36 are operated to disconnect block 30 from the apparatus, thus isolating in the block 30 the contaminants condensed therein. Once the sample block 30 has reached ambient temperature the block can be removed and a fresh one may be installed in its place for collecting a further sample, if desired. The samples collected in such blocks 30 can then be returned to a laboratory, or the like, where the blocks can be inserted into equipment of the type shown in FIG. 6, and then can be subjected to the heating cycle so as to deliver the previously captured sample to a GC oven or the like.

In connection with the apparatus described herein, it is important to note that the flow path of the sample gas is minimized, in that the material condensed from the sample gas is caused to travel the shortest entrance and exit paths in the apparatus. For example, the material that is condensed in the block 30 travels only from tubing T4 through the valve V4 and the tubing T2 to the block 30, where it is condensed before reaching T1. Then, when it is removed from the block 30, the flow of the carrier gas travels through valve V4, then T1, and in reverse order through block 30, tubing T2, the valve V4 and the tubing T5 to the analytical device. In other words, the condensed matter does not travel entirely through the apparatus, but merely one way into the block 30, and in the opposite direction out of the block to the analytical device.

From the foregoing it will be apparent that the present invention provides an improved method and apparatus for the separating out, and condensation or trapping of trace gaseous contaminants from atmospheric or similar gas samples, thereby considerably simplifying cyrogenic gas sampling procedures (CGSP). Incorporated in the system are both the condensation and heating functions necessary for laboratory sampling and analysis, or field sampling requirements. This improved CGS apparatus considerably reduces the size and the cost of the support equipment heretofore required when using cryogenic liquids for condensing trace contaminants from gaseous mixtures of the like, and utilizes common components adapted for use in both a laboratory setting and in the field. Samples stored in gaseous form in compressed air cylinders or sampling bags can be concentrated using the laboratory version of this invention. Conversely, samples collected in the field will be in modules completely compatible with the laboratory unit. Also, the means of collection of samples allows the determination of contaminants in the parts per trillion (v/v) range with greater ease then heretofore possible. Ultimate detection limit will depend on the analytical equipment, since the range of concentration of samples using this invention is determined by the amount of air sampled. For all practical purposes this will be determined solely by the sample block design and will be variable as requirements dictate. The parts per trillion range is a conservative estimate.

While this invention has been illustrated and described in detail in connection with only certain embodiments thereof, it will be apparent that it is capable of still further modification, and that this application is intended to cover any such modifications as may fall within the scope of one skilled in the art or the appended claims. For example, the electronic heat pumps obviously could vary in size and in number without departing from this invention, and the means for cooling the heat sink also could be supplemented or modified as desired. Moreover, although the valves disclosed herein have been described as being manually operable, they obviously could be electrically controlled, if desired. And although the sample blocks have been shown to be mounted on chips 15 and 16, obviously the blocks could be mounted between the chips, if desired.

We claim:

1. Apparatus for condensing out trace contaminates from gases, comprising:
   a heat sink having thereon a support surface,
   at least one thermoelectric element mounted on said heat sink and having thereon a first surface disposed in thermally conductive contact with said support surface on said heat sink,
   a sample block mounted on said element and having thereon a surface disposed in thermally conductive contact with a second surface formed on said element opposite said first surface thereof,
   said block having therein a contaminate collecting duct overlying said element and containing a plurality of condensing surfaces,
   means for operating said thermoelectric element in a chilling mode to reduce the temperature of said block and said condensing surfaces therein to a predetermined gas condensing temperature,
   means for conveying a gas sample in a first direction through said duct while the latter is at said gas condensing temperature, thereby to cause contaminates in said gas sample to be condensed out on said condensing surfaces,
   means for operating said thermoelectric element in a heating mode to vaporize contaminates previously condensed out in said duct on said condensing surfaces, and
   means for conveying a carrier gas through said duct in a second direction opposite to said first direction, thereby to convey said vaporized contaminates to a gas analytical device or the like.

2. Apparatus as defined in claim 1, including means for releasably supplying a compressive force to the members of the assembly represented by said heat sink, said thermoelectric element and said sample block, thereby to improve the thermally conductive contact between adjacent members in said assembly.

3. Apparatus as defined in claim 1, wherein
   said duct forms a serpentine path in said block, and
   said condensing surfaces comprise a plurality of small beads in said duct.

4. Apparatus as defined in claim 1, including means mounted adjacent said heat sink for conveying heat away therefrom during operation of said element in a chilling mode.

5. Apparatus as defined in claim 4, wherein said heat sink has a plurality of spaced fins formed thereon at the side thereof remote from said support surface, and said means for conveying heat away from said heat sink comprises a blower mounted adjacent said heat sink to blow cooling air between the fins thereof.

6. Apparatus as defined in claim 1, wherein said sample block comprises a length of copper tubing having a serpentine shaped portion thereof secured by a thermally conductive film to said second surface on said thermoelectric element.

7. Apparatus as defined in claim 1, wherein said sample block comprises a metal block having opposed, planar surfaces one of which is removably secured by a thermally conductive film to said second surface on said thermoelectric element, and said duct is formed in said block between said opposed, planar surfaces thereof.

8. Apparatus as defined in claim 1, including means removably securing said sample block on said element.

9. Apparatus for condensing trace contaminates from gases, comprising a sample block having therein a contaminate collecting duct means defining a plurality of condensing surfaces in said duct, a thermoelectric element mounted at one side in thermally conductive contact with said block and operable selectively to chill said block and the condensing surfaces in said duct to a predetermined temperature, pump means for conveying a gas sample of predetermined volume from a supply thereof in one direction through said duct when said condensing surfaces have been chilled to said predetermined temperature, thereby to cause contaminates in said sample to be condensed out on said condensing surfaces, means for operating said thermoelectric element in a manner to heat said block and to vaporize said contaminates previously condensed on said condensing surfaces, and means for conveying a carrier gas through said duct in a direction opposite to said one direction, and into a gas analyzer device, after vaporization of said contaminates by said thermoelectric element.

10. Apparatus as defined in claim 9, including a heat sink secured in thermally conductive contact with said thermoelectric element at the side thereof opposite said sample block.

11. Apparatus as defined in claim 9, wherein said pump means comprises, a chamber having a reference volume equal to the desired volume of the gas sample to be conveyed through said duct, a vacuum pump, and valve means operable momentarily to connect said pump to said chamber to evacuate the latter and create a vacuum therein, and thereafter operable to disconnect said pump from said chamber and to connect said chamber to said duct thereby to draw said gas sample in said one direction through said duct to said chamber.

12. Apparatus as defined in claim 11, wherein said valve means comprises a gas sampling valve interposed between said sample block and said pump means and adjustable between a sampling position in which said duct is connected at one end to said chamber and at its opposite end to said gas supply, and a transfer position in which said duct is connected at said one end thereof to said carrier gas and at said opposite end thereof to said gas analyzer device.

13. Apparatus as defined in claim 9, including means releasably clamping said sample block and thermoelectric element securely against stationary support, said stationary support comprising a heat sink having thermally conductive contact with the side of said thermoelectric element remote from said block.

14. A method of cryogenically trapping gas contaminates in a portable sample block for subsequent delivery to a gas analyzer device, comprising, providing a sample block having therein an elongate duct containing a plurality of condensing surfaces, removably securing said block against a thermoelectric element so that the engaged surfaces on said block and said element, respectively, are in thermally conductive contact with each other, applying voltage of a first polarity to said element to effect reduction of the temperature of said block and said condensing surfaces therein to a predetermined condensing temperature in the range of $-25°$ C. to $-90°$ C., and conveying a gas sample in a first direction through said duct after said block and condensing surfaces have reached said predetermined condensing temperature, thereby to cause contaminates in said gas sample to condense out onto said condensing surfaces.

15. The method as defined in claim 14, including sealing opposite ends of said duct in said block after condensing out the contaminates on said condensing surfaces, and removing said block from engagement with said thermoelectric element and replacing the removed block with a similar block.

16. The method as defined in claim 14, including after condensing out the contaminates in said duct, reversing the polarity of the voltage applied to said element thereby to cause said element to heat said block to effect vaporization of the previously condensed contaminates in said block, and conveying a carrier gas through said duct in a direction opposite to that of said first direction, and into a gas analyzer device thereby to convey said vaporized contaminates into said device.

* * * * *